(12) United States Patent
Bathen et al.

(10) Patent No.: US 8,287,274 B2
(45) Date of Patent: Oct. 16, 2012

(54) TOOL FOR ORTHODONTIC APPLIANCE

(75) Inventors: Juergen Bathen, McMinnville, OR (US); Rolf Hagelganz, Dundee, OR (US)

(73) Assignee: World Class Technology Corporation, McMinnville, OR (US)

( * ) Notice: Subject to any disclaimer, the term of this patent is extended or adjusted under 35 U.S.C. 154(b) by 141 days.

(21) Appl. No.: 12/800,926

(22) Filed: May 25, 2010

(65) Prior Publication Data
US 2011/0294088 A1 Dec. 1, 2011

(51) Int. Cl.
*A61C 3/00* (2006.01)
(52) U.S. Cl. .............................. 433/10; 433/3
(58) Field of Classification Search .................. 433/3, 4, 433/10, 11; 81/6, 436, 460, 461; 411/405, 411/407, 410, 919
See application file for complete search history.

(56) References Cited

U.S. PATENT DOCUMENTS

| | | | | |
|---|---|---|---|---|
| 4,171,568 A | * | 10/1979 | Forster | 433/10 |
| 4,561,844 A | * | 12/1985 | Bates | 433/14 |
| 5,492,040 A | * | 2/1996 | Bellas | 81/125.1 |
| 5,743,737 A | * | 4/1998 | Hawn et al. | 433/141 |
| 5,862,725 A | * | 1/1999 | Negus | 81/461 |
| 2006/0086214 A1 | * | 4/2006 | Smed | 81/461 |
| 2007/0259304 A1 | * | 11/2007 | Hagelganz et al. | 433/10 |
| 2009/0004618 A1 | * | 1/2009 | Oda et al. | 433/24 |
| 2011/0081622 A1 | * | 4/2011 | Mashouf | 433/10 |

* cited by examiner

*Primary Examiner* — Cris L Rodriguez
*Assistant Examiner* — Eric Rosen
(74) *Attorney, Agent, or Firm* — Chernoff, Vilhauer, McClung & Stenzel, LLP

(57) ABSTRACT

An orthodontic tool for an orthodontic appliance includes a handle and at least one distal end having a finger. The finger has a manipulator, which may include a pin or a plurality of pins, and a probe for engaging a rotary archwire cover. Using the tool, the orthodontist may open and close the archwire cover, which is rotationally mounted to an orthodontic bracket.

3 Claims, 5 Drawing Sheets

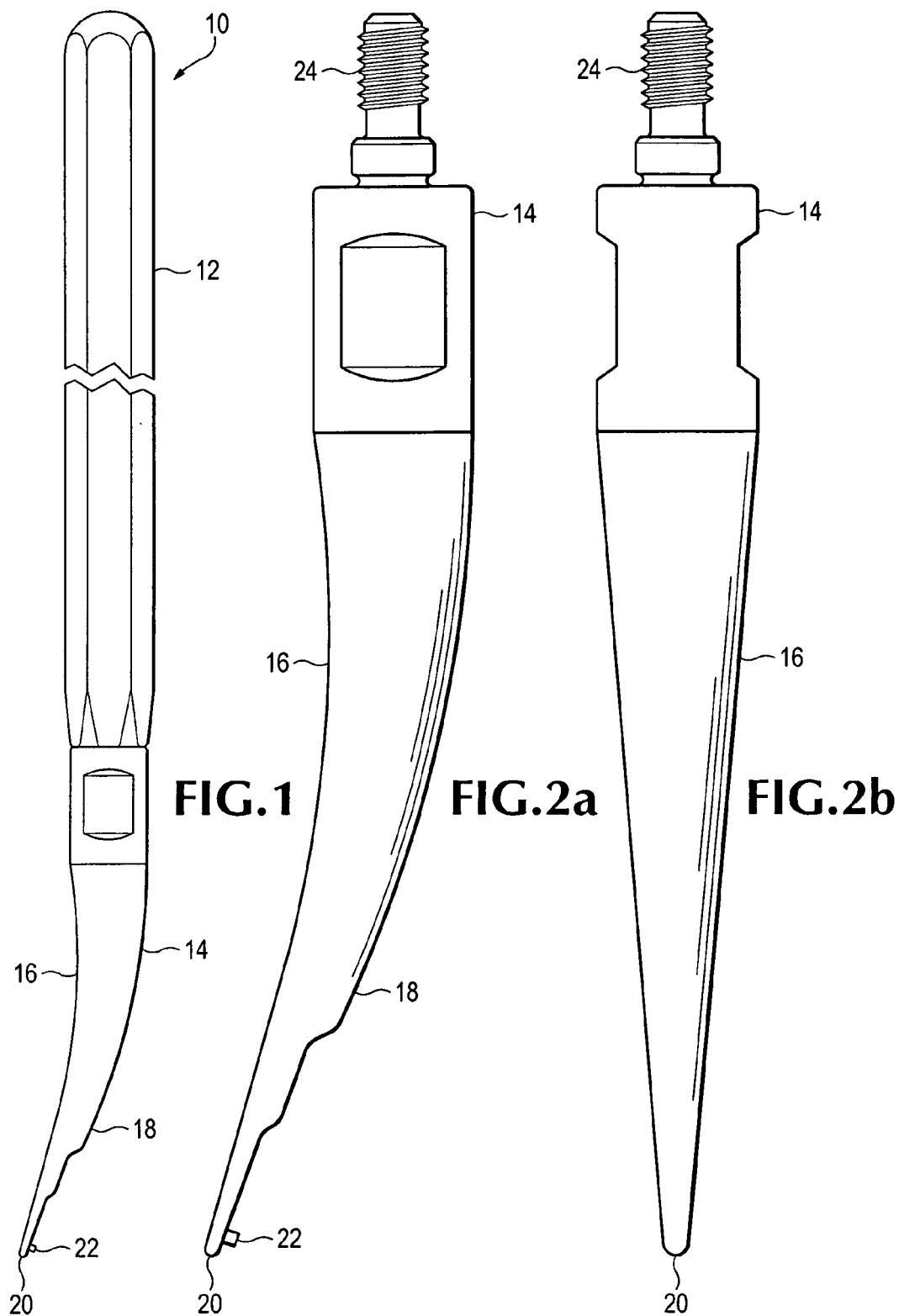

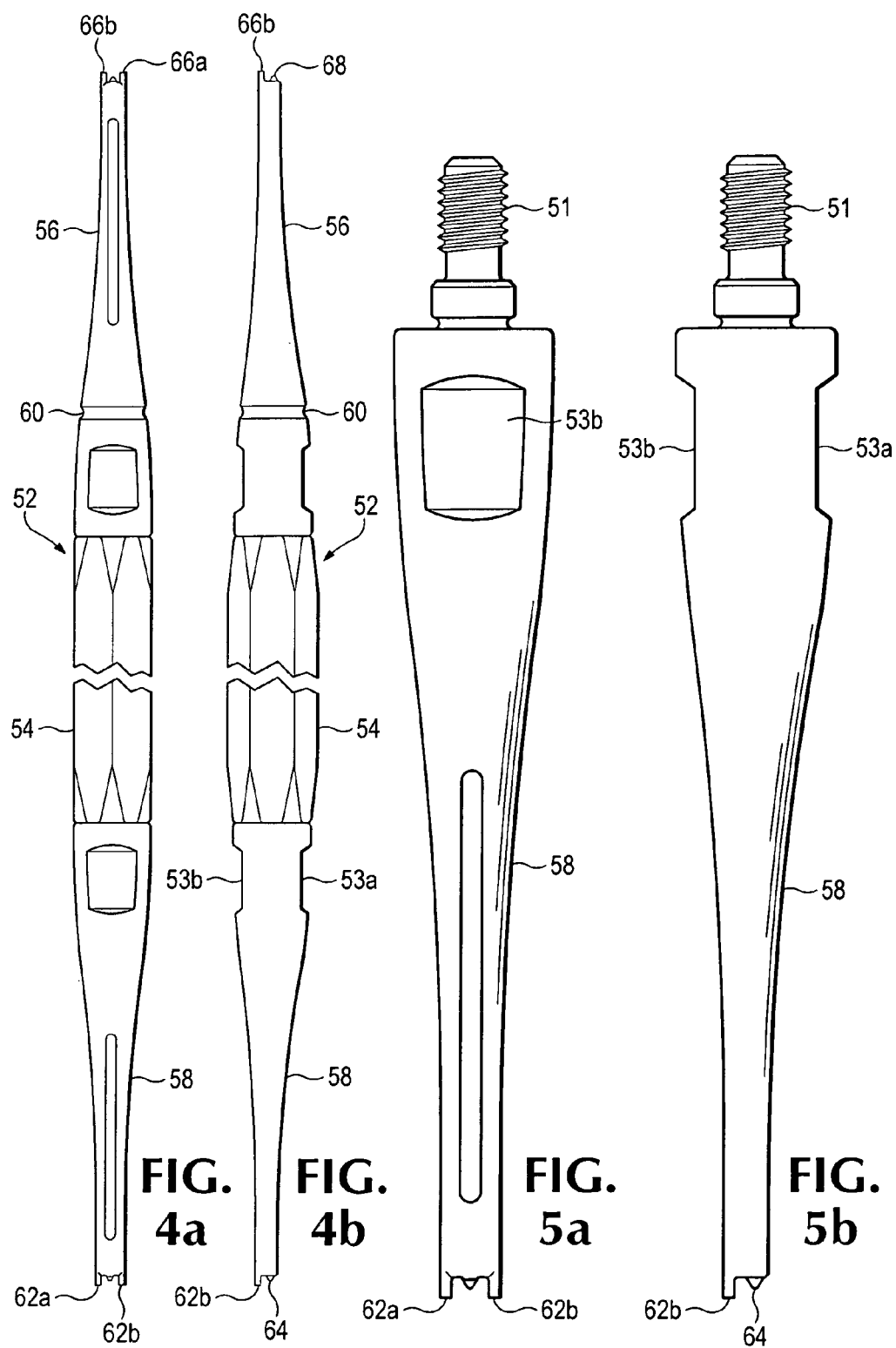

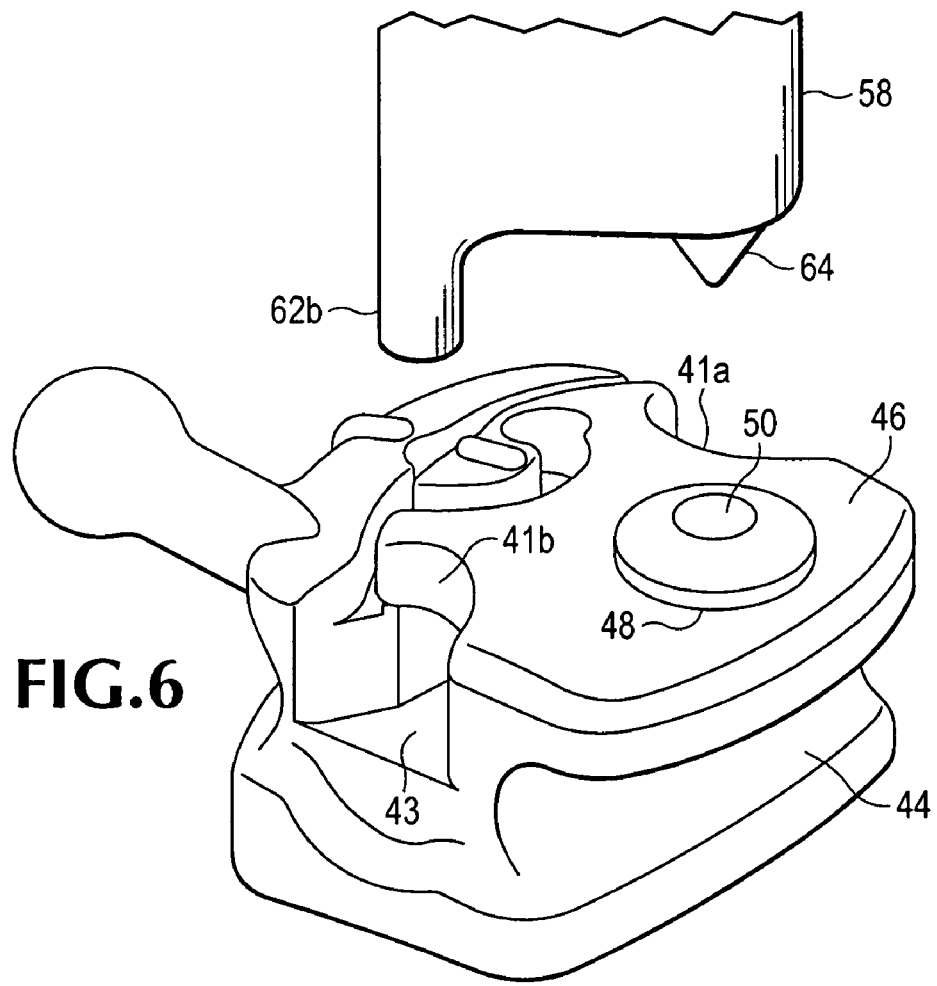
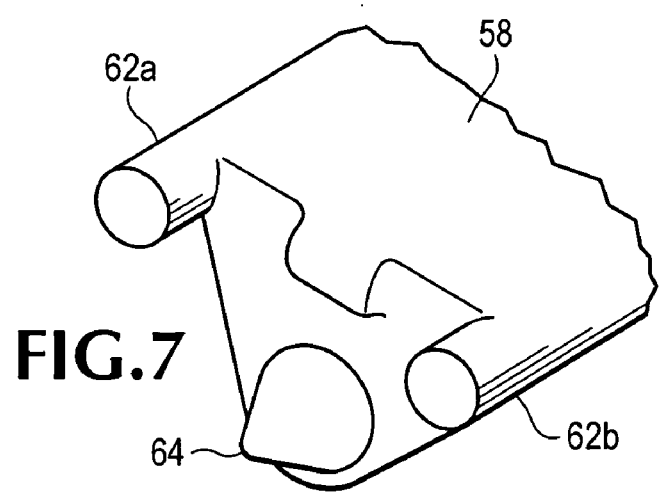

TOOL FOR ORTHODONTIC APPLIANCE

CROSS-REFERENCE TO RELATED APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

Field of the Invention

Certain orthodontic appliances or brackets employ an archwire slot for receiving a thin archwire. The archwire is typically a curved metallic wire having a rectangular or circular cross-section that is bent or twisted prior to engagement by the brackets. Certain types of brackets employ covers, which move across the archwire slot, to retain the archwire therein. A particular type of orthodontic appliance that uses a rotary cover is shown in U.S. patent application Ser. No. 11/788,840 (publication no. US2007/0259304). This application is incorporated by reference herein and shows a self-ligating orthodontic bracket mountable on the surface of a tooth and sized for receiving an orthodontic archwire. A rotary ligating cover, which is selectively rotatable between an open position permitting access to the archwire slot and a closed position covering the archwire slot and having one or more locking features for holding the rotary cover in a closed position, is shown in this application.

The orthodontic brackets of this type are small and manipulation of the locking rotary cover is a difficult task. While conventional dental tools can be used to open and close a rotary cover of this type, this particular orthodontic bracket design is unique and, heretofore, tools have not existed that are designed for the express purpose of manipulating a rotationally-mounted archwire cover of this type. In order for an orthodontic bracket having a rotary archwire cover to be practical, a tool must be provided that will enable the orthodontist to quickly and easily open and close the rotary cover mechanism that is employed to retain the archwire in its slot.

BRIEF SUMMARY OF THE INVENTION

An orthodontic tool for an orthodontic appliance includes a handle and at least one distal end having a finger. The finger has a manipulator, which may include a pin or a plurality of pins, and a probe for engaging a rotary archwire cover. Using the tool, the orthodontist may open and close the archwire cover, which is rotationally mounted to an orthodontic bracket.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 1 is a side-elevation view of one embodiment of an orthodontic tool.

FIG. 2a is a side-elevation view of a detachable finger portion of the tool of FIG. 1.

FIG. 2b is a side elevation view of the finger portion in FIG. 2a rotated 90°.

FIG. 4a is a side-elevation view of a second embodiment of an orthodontic tool.

FIG. 4b is a side-elevation view of the orthodontic tool of FIG. 4a rotated 90°.

FIG. 5a is a side-elevation view of a finger portion of the tool of FIG. 4a.

FIG. 5b is a side-elevation view of the tool of FIG. 4a rotated 90°.

FIG. 6 is a partial perspective view of the tool of FIG. 4a positioned to engage an orthodontic bracket.

FIG. 7 is a partial perspective view of the tip of the orthodontic tool of FIG. 4a.

DETAILED DESCRIPTION OF PREFERRED EMBODIMENT

Figure 3:
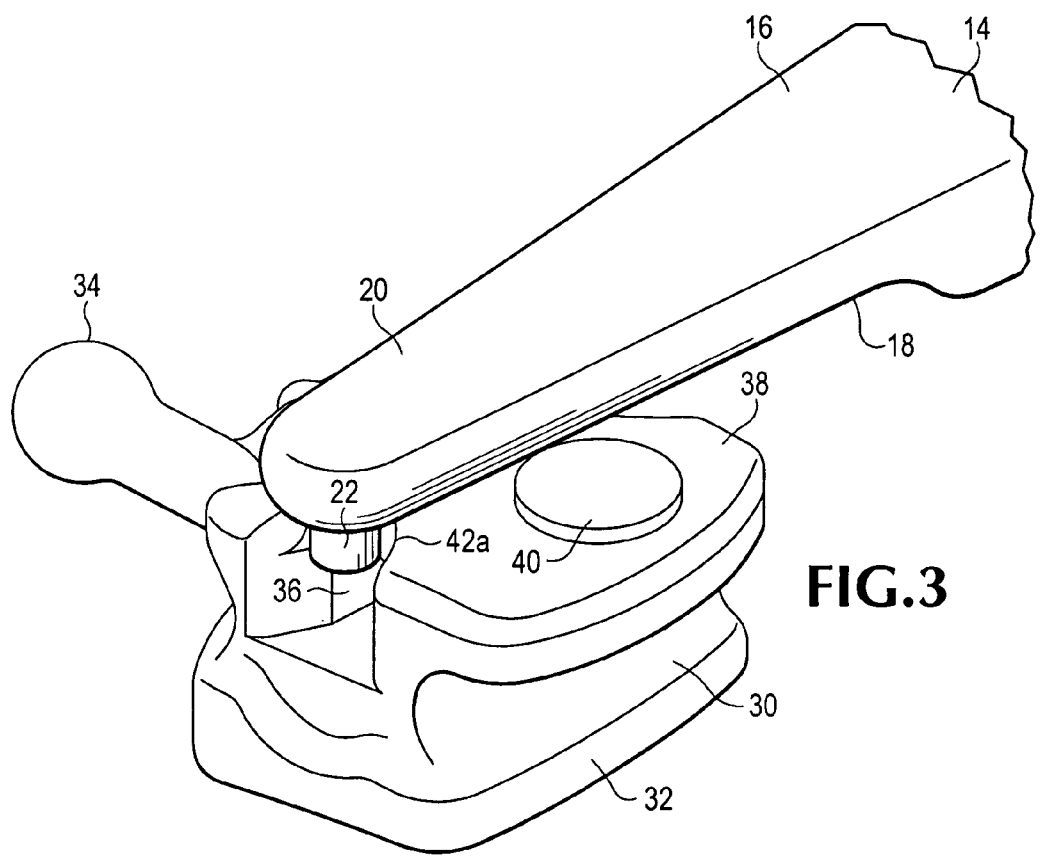
FIG. 3 is a partial perspective view of the tool of FIG. 1 engaging an orthodontic bracket.

An orthodontic tool is provided for manipulating an archwire closure mechanism on an orthodontic appliance of the type that employs a rotationally mounted archwire closure. The tool includes a thin, elongate handle portion having a longitudinal axis and a finger portion, which is detachably coupled to the handle.

According to a first embodiment of an orthodontic tool, opposed finger portions are detachably coupled to an elongate handle at either end along the axis. Each finger has a triangularly-shaped tip region. Two legs of the triangle constitute cylindrical pins and the apex of the triangle supports a projecting member, which may be in the form of a conical probe. The two side-by-side pins engage concave indentations on either side of a rotary archwire cover while the conical probe fits into a similarly shaped indentation in an axial pin which secures the rotary cover to an orthodontic bracket. Thus by twisting the handle with the fingers, a rotary motion is imparted to the rotary cover enabling the orthodontist to open or close the cover over the archwire slot. The handle itself has a surface comprised of intersecting flat planes to provide a non-slip gripping surface for the orthodontist's thumb and fingers. The tool has two fingers, one at each end. Because brackets on the lower interior teeth are smaller, one of the detachable fingers has closer spacing between the cylindrical pins and the conical probe than the finger at the other end of the tool. A colored band may be used on one of the fingers to identify it as the end having the smaller dimensions.

In a second embodiment, the finger portion has an axis that curves laterally away from the longitudinal axis of the handle portion. The distal end of the finger portion includes a tip, which has a cylindrical pin that extends substantially perpendicular to a line tangent to the curved axis of the finger portion in a "downward" direction. The finger portion is curved in an "upward" direction. Therefore, the cylindrical pin extends outwardly from the convex lower surface of the finger portion. This curvature enables the tool to easily engage rotary closure mechanisms on brackets installed on a patient's teeth. Further, the finger portion has a lower surface that tapers in a step-wise fashion becoming thinner toward the distal end of the finger. In addition, the width of the finger is tapered toward the distal end so that the finger is thickest where it joins the handle portion and thinnest at the tip where the cylindrical pin is located. The step-wise taper comprises at least one undercut or relieved area adjacent the tip of the finger portion. This makes the tip of the finger portion thin enough to clear the surface of the bracket and engage the relatively small rotary closure mechanism of the bracket.

Referring to FIGS. 1 and 2, an orthodontic tool 10 includes an elongate handle portion 12 and a detachable finger portion 14. The finger portion 14 has a top surface 16 and a bottom surface 18. The finger portion 14 has a tip 20. A cylindrical pin 22 is mounted at the tip 20 and extends in a downward direction away from the bottom surface 18. The bottom surface 18 has a convex curvature and is tapered in step-wise fashion toward the tip 20. The thickness of the tip 20 is cut away along the bottom surface 18 to create relieved areas so as to penetrate small volumes within the mouth of a patient. As shown best in FIG. 2, the finger portion 14 may be detachably coupled to the handle 12 by way of screw threads 24.

In addition to the taper in thickness of the finger portion 14, the width of the finger portion 14 is also tapered from adjacent the handle 12 to the tip 20. This taper is best shown in FIG. 2b in which the top surface 16 shows a linear taper of gradually decreasing width.

The use of the tool with a bracket having a rotary archwire cover is shown best in FIG. 3. A bracket 30 has a base 32, which is affixed to a patient's tooth (not shown). The bracket 30 may include a tie-wing 34 and has an archwire slot 36. An archwire (not shown) extends through the slot between adjacent brackets of the same type. The bracket 30 is of the type shown in the aforementioned U.S. patent application Ser. No. 11/788,840. As such, the bracket 30 has a top cover 38, which is mounted rotatably on a pin 40 that extends into the bracket in a direction substantially perpendicular to the direction of the archwire and the archwire slot 36. The top cover 38 has a pair of concave indentations on either side of the cover 38 (only indentation 42a is shown). The cylindrical pin 22 is sized to fit the indentation 42a so that pressure exerted by the orthodontist, either in a push or a pull direction (from the opposite side), will open or close the rotary cover 38.

In a preferred embodiment of the invention shown best in FIG. 6, the bracket 44 has a rotary top cover 46, which is in all respects similar to the rotary bracket 30, but in addition, the rotating cover is journalled on an axial pin 48, which has an indentation 50 that may be inversely conical in shape. The cover 46 has concave indented sides 41a and 41b.

Referring to FIGS. 4a and 4b, a tool 52 includes a handle portion 54. The handle may be grasped like a pencil and, for ease of manipulation, may be an octagonally-shaped cylinder. The eight flat sides of the handle 54 enable the user to easily twist the handle 54 to manipulate the rotary cover 46. Two fingers, 56 and 58, are attached to the handle at either end. The finger 56 has a colored band or other indicia 60, which identifies it as dimensionally smaller than the finger 58. Thus, the finger 56 is intended to be used on brackets secured to the lower interior teeth, which are typically smaller brackets, and the finger 58 is intended to be used on all other brackets.

The finger 58 has a distal tip portion 60, which includes a pair of cylindrical pins 62a and 62b. The tip 60 also includes a probe 64, which has a conical shape. The probe 64 and the cylindrical pins 62a and 62b are manipulators, which engage the rotary cover 46 of the orthodontic bracket 44. The opposing finger 56 includes pins 66a and 66b with a probe 68. The pins 66a and 66b are spaced closer together because the finger 56 is for smaller brackets which have a closer spacing.

Figure 8:
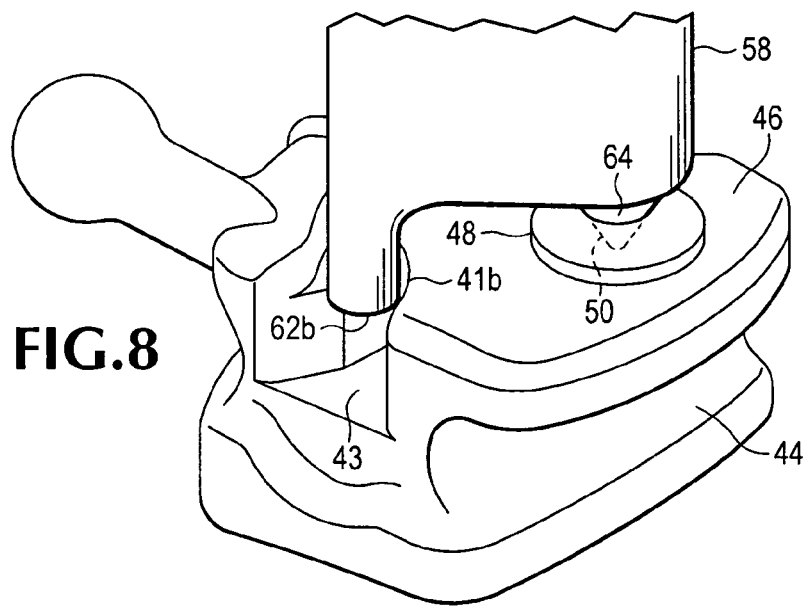
FIG. 8 is a partial perspective view of the tip of the tool of FIG. 4a engaging an orthodontic bracket when the archwire cover is closed.
Figure 9:
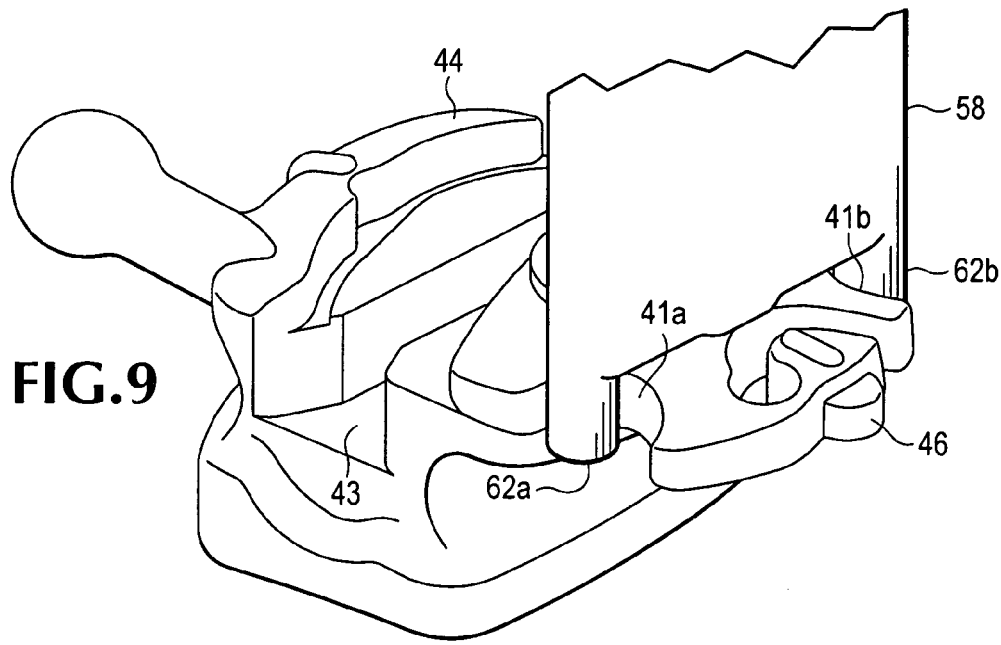
FIG. 9 is a partial perspective view of the tip of the tool of FIG. 4a engaging the orthodontic bracket of FIG. 8 when the archwire cover is open.

As shown best in FIG. 7, the pins 62a and 62b together with probe 64 are arranged in a triangular array. The probe 64 engages the recess 50 on the pivot pin 48 (see FIG. 8). At the same time, the pins 62a and 62b engage concave indentations 41a and 41b on the cover 46 of the bracket 44.

The cover 46 may be rotated around its axial pin 48 by twisting the tool held by the thumb and forefinger about its longitudinal axis. This motion exposes the archwire slot 43 or closes the cover 46 over it. The pins 62a and 62b are sized to slide through the archwire slot 43 when the tool 52 is rotated. The triangular array of the two pins and the probe provide maximum leverage and firm control for rotating the cover with little effort. In this way, the orthodontist can quickly and easily open and close the rotary cover over the archwire slot.

As shown in FIGS. 5a and 5b, the fingers (only finger 58 is shown) are attached to the handle 54 by screw threads 51. For ease of manipulation, thickened sides adjacent the threads 51 have indentations 53a and 53b so that the finger 58 may be easily attached to the handle 54.

The manipulators 62a, 62b and 64 may have any desired shape. That is, pins 62a and 62b need not be cylindrical but could be, for example, hemispherical. Further, the conical probe 64 could be any shape that mates effectively with a complementary shaped depression in the axial pin 48.

The terms and expressions employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. In combination, an orthodontic appliance adapted to be affixed to the surface of a patient's tooth, said appliance having an archwire slot for receiving an archwire and having a rotary cover mounted for rotation about an axial pin between an open position exposing the archwire slot and a closed position covering the archwire slot, the axial pin being oriented perpendicular to the surface of the tooth, and a tool for opening and closing said cover, said tool having a substantially straight handle having a longitudinal axis and manipulator members at a distal end for engaging said cover wherein said cover includes concave indented side portions and said manipulator members include pins that engage said concave indented side portions, whereby the handle is aligned with said axial pin when said manipulator members are in engagement with said cover, whereby said cover is opened and closed by twisting said tool about its longitudinal axis.

2. The combination of claim 1 wherein said manipulator members include a central probe which engages a depression in said axial pin.

3. In combination, an orthodontic appliance adapted to be applied to the surface of a tooth and a manipulating tool for said appliance,
  (a) said orthodontic appliance comprising a base and a body portion, said body portion having an archwire slot, and a rotary cover selectively rotatable on an axis substantially perpendicular to said tooth to cover and expose said archwire slot, said cover having concave indentations on sides of the cover facing opposing directions;
  (b) said manipulating tool having an elongate handle and a distal end having a finger, the finger including a pair of side by side pins adapted to engage said concave indentations simultaneously.

* * * * *